United States Patent [19]

Cooper

[11] Patent Number: 5,087,253
[45] Date of Patent: Feb. 11, 1992

[54] COMBINATION DIAPER TRAINING PANT FOR ADULTS AND CHILDREN

[76] Inventor: Rosanna M. Cooper, P.O. Box 31869, Aurora, Colo. 80041

[21] Appl. No.: 876,767

[22] Filed: Jun. 20, 1986

Related U.S. Application Data

[63] Continuation-in-part of Ser. No. 550,969, Nov. 14, 1983, Pat. No. 4,615,695.

[51] Int. Cl.⁵ .............................................. A61F 13/15
[52] U.S. Cl. ................................................... 604/385.1
[58] Field of Search ............... 604/385 A, 385 R, 386, 604/393, 394, 397, 398, 399, 389-391, 385.1

[56] References Cited

U.S. PATENT DOCUMENTS

| | | | |
|---|---|---|---|
| 1,971,606 | 8/1934 | Grant | 604/376 |
| 2,525,396 | 10/1950 | Brennan | 604/386 |
| 2,649,858 | 8/1953 | LeBolt | 604/389 |
| 2,691,376 | 10/1954 | Tunnell | 604/386 |
| 2,834,347 | 5/1958 | Connally | 604/389 |
| 2,969,065 | 1/1961 | Farnsworth | 604/386 |
| 3,089,494 | 5/1963 | Schwartz | 604/389 |
| 3,599,640 | 8/1971 | Larson | 604/394 |
| 3,842,837 | 3/1974 | Sward | 604/385.1 |
| 4,036,233 | 7/1977 | Kozak | 604/370 |
| 4,122,552 | 10/1978 | Tedford | 604/389 |
| 4,145,763 | 3/1979 | Abrams et al. | 604/391 |
| 4,205,679 | 6/1980 | Repke et al. | 604/394 |
| 4,205,679 | 6/1980 | Repke et al. | 604/394 |
| 4,500,316 | 2/1985 | Damico | 604/389 |
| 4,610,680 | 9/1986 | LaFleur | 604/385. |
| 4,615,695 | 10/1986 | Cooper | 604/394 |

FOREIGN PATENT DOCUMENTS 2559037  8/1985  France ...................... 604/385.1

*Primary Examiner*—C. Fred Rosenbaum
*Assistant Examiner*—Sharon Finkel
*Attorney, Agent, or Firm*—Timothy J. Martin

[57] ABSTRACT

An incontinent garment in the form of a universal combination diaper/training pant for children and adults is disclosed. The combination may be made in a one-piece configuration which would be disposable and may also be made in a two-piece configuration which would be washable. An outer water-resistant portion is formed in the shape of a pair of training pants and has an inner water-absorbing portion attached or positioned on the outer portion. An inner padding is positioned between the outer water-resistant portions and the inner water-absorbing portion.

When formed thusly the combination diaper/training pant may be used universally by children as well as adults and may be used as a diaper and/or training pant without requiring the necessity of stocking both types of garments. By varying the basic size of the novel configurations, all sizes from infants to adults can be made using the same structure, thus requiring a minimum of merchandise stocking for different types of garments.

1 Claim, 4 Drawing Sheets

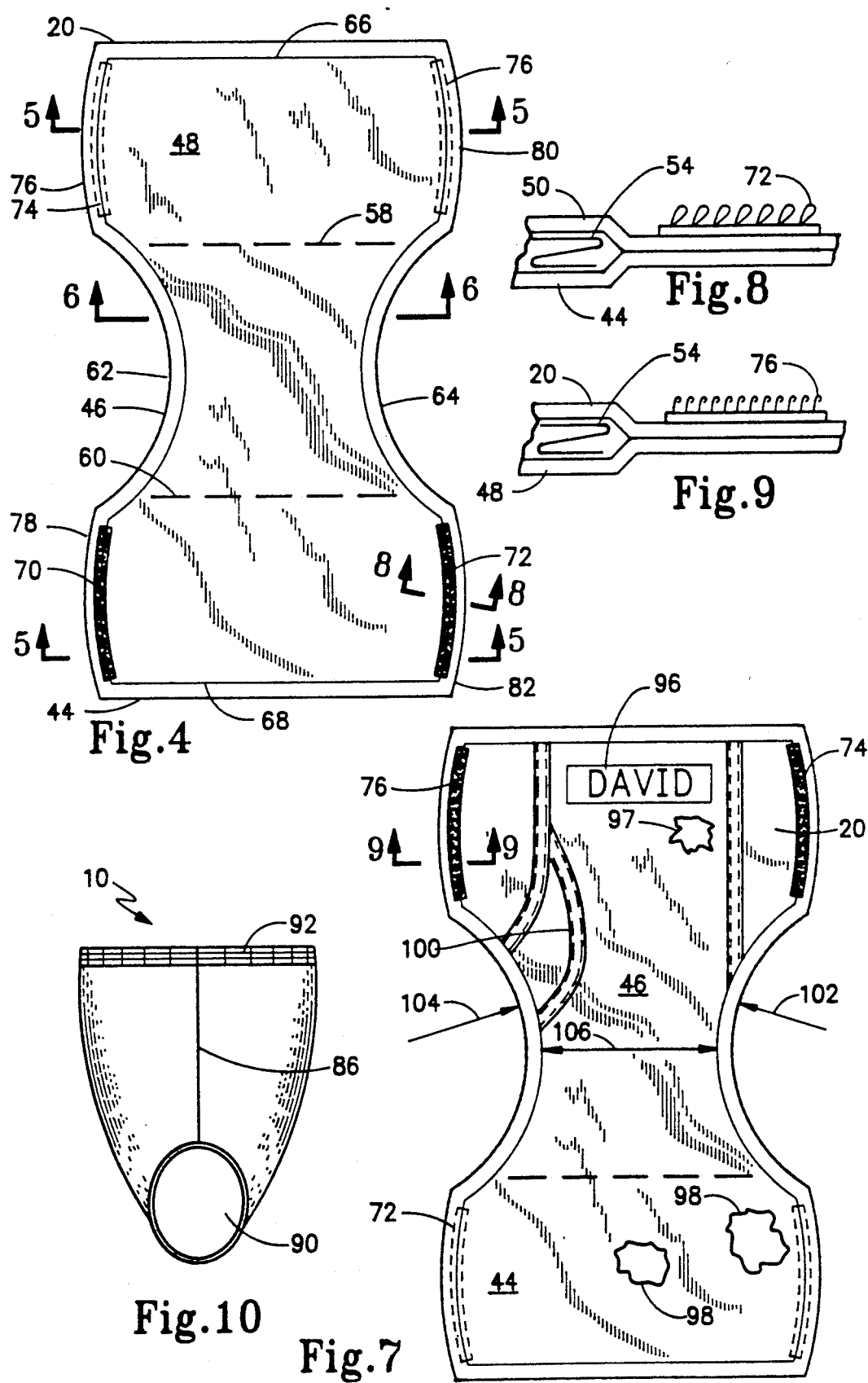

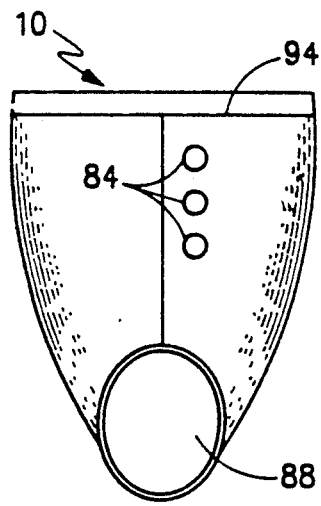
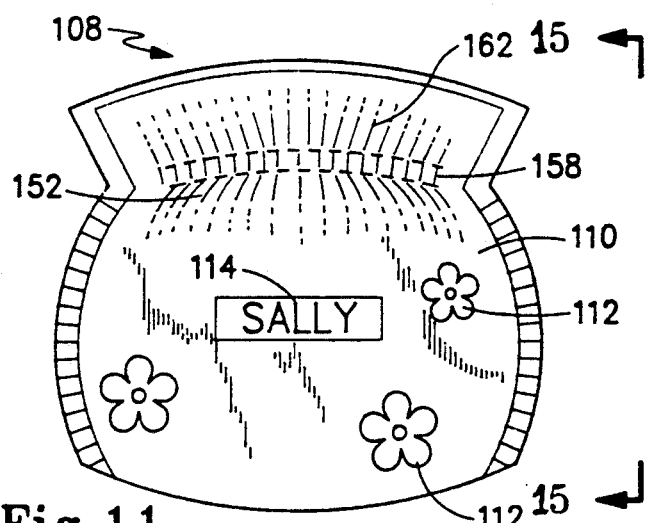
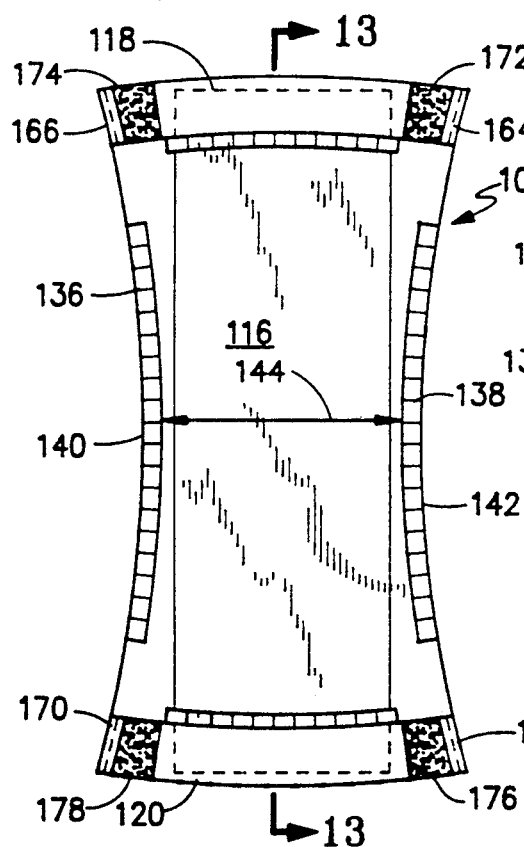
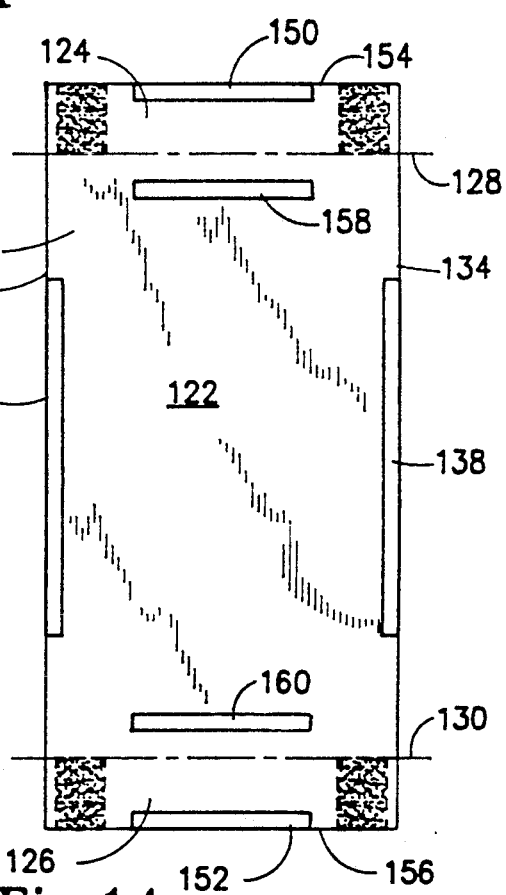
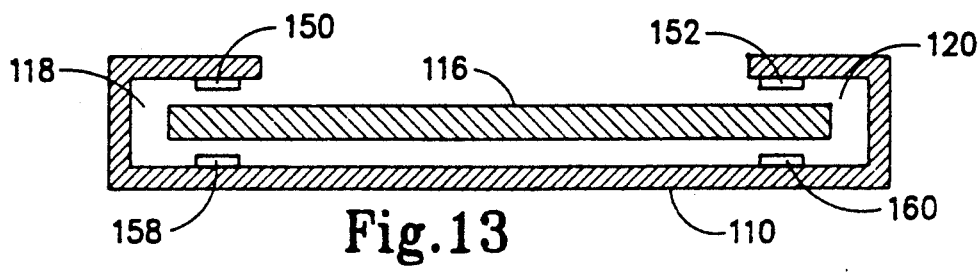

COMBINATION DIAPER TRAINING PANT FOR ADULTS AND CHILDREN

BACKGROUND OF THE INVENTION

This application is a continuation-in-part of my application Ser. No. 550,969 filed Nov. 14, 1983, issued as U.S. Pat. No. 4,615,695 on Oct. 7, 1986.

This invention relates generally to sanitary garments and more particularly to a universal combination diaper/training pant that may be used for infants, children and adults.

It is known to provide disposable diapers for infants having construction with varying thicknesses of a disposable material generally made in a rectangular form for positioning on the infant's body. It is also known to provide washable diapers for infants formed of cotton or some other water-absorbing material which is generally formed in the standard triangular shape.

Whenever an infant progresses from the stage of diapers to training pants, the parent must then stock a separate supply of lightweight training pants which are generally formed from some washable material over which would be positioned a plastic outer water-resistant pant. The training pant combination thus described would be used generally during the daytime for the child undergoing potty training. At nighttime the parent usually would return the child to a diaper for better moisture control, thus requiring a stocking of both a supply of diapers as well as a supply of training pants and outer waterproof garments. It is also known that adults, especially older adults, may have the need for a combination garment which can be used as an incontinence device for those having that problem. In addition, many mentally retarded children, young adults and adults have an incontinence problem requiring a special garment for their use. Many adults, even though elderly or retarded, would balk at the use of a standard diaper of either the throwaway type or washable type for solving their problem.

Incontinence pants are taught in the U.S. Pat. No. 4,338,939, issued July 13, 1982, to Helenne Deville. Various other sanitary garments are also taught in the U.S. Pat. No. 3,182,661, issued May 11, 1965, to L. P. Rireiro et al and in the U.S. Pat. No. 3,575,175, issued Apr. 20, 1971, to Mary H. McGuire.

Disposable panty shields are taught in the U.S. Pat. No. 3,463,154, issued Aug. 26, 1986 to L. A. Hendricks and in the U.S. Pat. No. 3,044,467, issued July 17, 1962, to L. E. Campau. A sanitary napkin holder is taught in the U.S. Pat. No. 2,840,078, issued June 24, 1958, to C. I. Smith.

Catamenial devices are taught in the U.S. Pat. No. 2,104,423, issued Jan. 4, 1938, to J. L. Hughes as well as in the U.S. Pat. No. 2,074,936, issued Mar. 23, 1937, to P. L. Paterson.

Further catamenial bandages are shown in the U.S. Pat. No. 1,192,439, issued July 25, 1916, to L. W. Luellen and in the U.S. Pat. No. 1,054,619, issued Feb. 25, 1913, to W. G. Robey.

Further catamenial devices are taught in the U.S. Pat. No. 4,031,897, issued June 28, 1977, to A. Graetz as well as in the U.S. Pat. No. 2,745,405, issued May 15, 1956, to A. M. Landy et al.

Other constructions of various pants and pant holders are taught in the U.S. Pat. No. 4,351,340, issued Sept. 28, 1982, to S. A. McLeod as well as in the U.S. Pat. No. 1,971,671, issued Aug. 28, 1934, to B. S. Alsop. Further holders for absorbent pads are taught in the U.S. Pat. No. 3,900,032, issued Aug. 19, 1975, to 0. T. Heurlen as well as in the U.S. Pat. No. 2,817,338, issued Dec. 24, 1957, to J. R. Slusser.

Other types of waterproof shield or holders are taught in the U.S. Pat. No. 2,711,736, issued June 28, 1955, to M. Petippas. Various diaper combinations are taught in the U.S. Pat. No. 3,890,973, issued June 24, 1975, to A. K. Davis et al and in the U.S. Pat. No. 4,037,602, issued July 26, 1977, to J. R. Hawthorne. The U.S. Pat. No. 3,192,926, issued July 6, 1965, to H. L. Callaghan teaches a hygenic diaper and the U.S. Pat. No. 3,860,003, issued Jan. 14, 1975, to Kenneth B. Buell teaches a disposable diaper combination.

Various fastening means for diaper sides are taught in the U.S. Pat. No. 3,646,937, issued Mar. 7, 1972, to D. A. Gellert as well as in the U.S. Pat. No. 3,967,622, issued July 6, 1976, to T. Cepuritis. Other fastening tabs are taught in the U.S. Pat. No. 3,920,016, issued Nov. 18, 1976, to F. K. Mesek et al and in the U.S. Pat. No. 3,848,594, issued Nov. 19, 1974, to K. B. Buell.

Material construction combinations for water-absorbing materials are taught in the U.S. Pat. No. 3,554,863, issued Jan. 12, 1971, to L. R. B. Harvey et al and in the U.S. Pat. No. 3,554,862, issued Jan. 12, 1971, to L. R. B. Harvey et al. A further combination structure for absorbing materials is taught in the U.S. Pat. No. 4,041,951, issued Aug. 16, 1977, to L. H. Sanford. The manufacture of various diaper combinations is taught in the U.S. Pat. No. 4,081,301, issued Mar. 8, 1978, to K. B. Buell and in the U.S. Pat. No. 4,261,782, issued Apr. 14, 1981, to R. R. Teed. An apparatus for compressing and banding large numbers of articles is taught in the U.S. Pat. No. 4,074,508, issued Feb. 21, 1978, to Phillip L. Reid.

None of the before-mentioned patents or prior arts teach the applicant's new and novel combination of a universal combination diaper/training pant which may be used for infants, children and adults.

SUMMARY OF THE INVENTION

In order to overcome problems inherent in the use of prior art type diapers, training pants, catamenial devices and others hereinbefore described, there has been provided by the applicant's invention a new and novel incontinent garment in the form of a universal combination diaper/training pant which may be used for infants, children and adults. The combination may be made in a one-piece configuration and in a two-piece configuration and may be made either disposable or washable or a combination of both. The applicant's novel combination uses an outer water-resistant portion shaped like a pair of training pants with an inner water-absorbing portion, also shaped like a pair of training pants. An inner padding is positioned between the outer water-resistant portions and the inner water-absorbing portion and serves to soak up urine from the person using the device. When formed in a one-piece configuration which is disposable, the production blank for the combination would be formed in generally hourglass configuration and may be formed as one or more layers of inner padding which are joined to the outer water-resistant portions. This pant type device may also be formed with side fastening means such as double-sided tape, snaps or Velcro type fasteners. Multiple parallel rows of tape may be provided to permit adjustable sizes and to permit selected reattachment of the pant after removal.

The applicant's combination diaper/training pant may also be manufactured in a two-piece washable combination having an outer water-resistant portion which is washable and has distinctive decorative features caused by the novel construction of the outer portion. An inner, separate, water-absorbing pad would be positioned within pockets formed in the outer portion and the inner pads may also be washable or may be disposable at the option of the purchaser.

Indicia may be positioned on the outer water-resistant portion of each of the combinations and the outer portion may also be formed in various colors as well as being formed from white plastic-type material within the spirit and scope of the invention. The user's name may be applied to the outer portion of the various combinations as desired and other indicia may also be attached to the outer portion to make the combination mare pleasing to the person using the device.

With the applicant's novel invention, separate diapers and training pants as well as outer waterproof garments are not required to be purchased and stocked by the parent. A single combination diaper/training pant is usable for all ages from infants to adults simply by purchasing a larger size garment as the person progresses in age and requires the garment.

Further, the present invention specifically provides a disposable training pant for persons older than infants. To accomplish this the hourglass configuration, when secured for use, defines leg openings that have planes at an angle of approximately 45 degrees to the vertical axis of the pants. This orientation avoids bunching or bagging of the pant between the legs of the wearer. Elastic bands completely surrounds the leg openings. In the case of a male user, a front fly opening is provided in the outer water-resistant layer, and the inner pad is formed by a pair of absorbent layers each having a fly opening. The opening of the inner layer next to the outer layer coextensive with the outer opening and the opening of the other inner layer being offset from the other two fly openings.

Accordingly, it is an object and advantage of the invention to provide a universal washable or disposable combination diaper/training pant which may be used by infants, younger children and adults such as elderly having incontinence problems as well as mentally retarded and others having incontinence problems.

Yet another object and advantage of the invention is to provide a new and novel combination garment which may be used by all ages and may have decorative indicia placed on the garment to personalize it.

Still yet another object and advantage of the invention is to provide a new and decorative garment for use by females which is washable and has a separate inner liner which may be disposable or washable according to the type of liner positioned in the garment.

A further object and advantage of the invention is to provide a new and novel universal combination diaper/training pant configuration that is usable for all sizes of persons and may simply be manufactured in one basic shape with increased size of the shape to fit various size persons and which shape is more comfortable to wearer.

It is still a further object of the present invention to provide an incontinence pant that substantially resembles a standard underpant in appearance and feel and which may be detached to permit waste elimination and reattached for continued wear.

These and other objects and advantages of the invention will become apparent from a study of the drawings and from a review of the specification following hereinafter describing the preferred embodiment which has been given by way of illustration only.

BRIEF DESCRIPTION OF THE DRAWINGS

FIG. 4 is a plan view of the production blank for the applicant's novel combination;

FIG. 7 is a plan view of the outside of a production blank for the applicant's new and novel combination;

FIG. 8 is a partial sectional view, taken along line 8—8 of FIG. 4;

FIG. 9 is a partial sectional view, taken along line 9—9 of FIG. 7;

FIG. 10 is a side view of the applicant's one-piece disposable combination when formed in a sewn side-seam construction;

FIG. 10A is a side view of a modification of the applicant's one-piece disposable combination when formed with side fastening such as snaps;

FIG. 11 is a front view of the applicant's new and novel two-piece washable combination;

FIG. 12 is a plan view of the inside of the appliant's combination shown in FIG. 11 showing the separate insertible padding within pockets formed in the combination;

FIG. 13 is a cross-sectional view, taken along line 13—13 of FIG. 12;

FIG. 14 is a plan view of the production blank for the outer washable portion of the applicant's invention shown in FIG. 11;

DESCRIPTION OF THE PREFERRED EMBODIMENT

Figure 1:
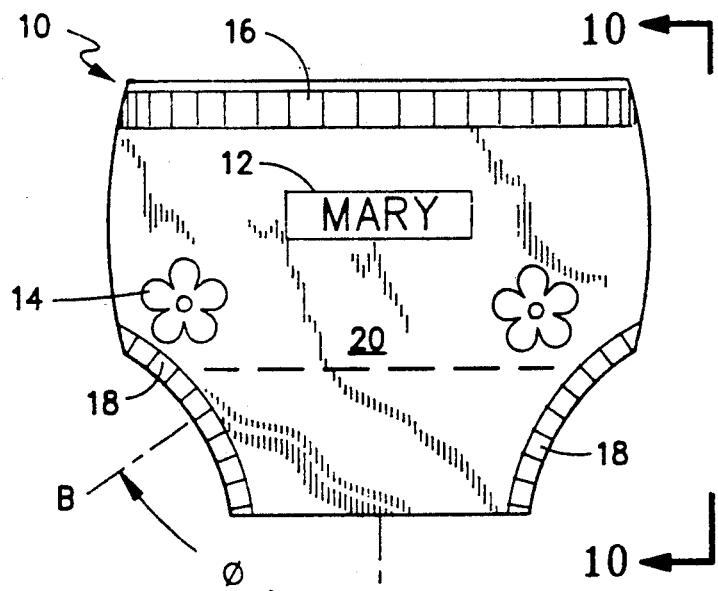
FIG. 1 is a side view of the applicant's combination diaper/training pant made in a one-piece disposable configuration.

Referring now to the drawings in general and in particular to FIG. 1 of the drawings there is shown a side view of the applicant's incontinent garment in the form of a combination diaper/training pant made in a one-piece, disposable configuration generally by the number 10. Thus, for purposes of this description the term "combination diaper/training pant" may be taken to refer to an incontinent garment adapted to be worn on the body against the skin. The combination diaper/training pant shown in FIG. 1 may have contained on the outside thereof indicia 12 designating the person's name and also may contain indicia 14 designating flowers or some other suitable object. An elastic top 16 is used to gather the top for a resilient tight fit on the body of the user along with elastic leg openings 18 in the lower portion of the diaper 10. The outer surface 20 of the combination may be formed of plastic, laminated plastic or some other suitable material and may also be formed of vinyl. The color of the outer surface 20 may be white or a solid color or a combination of colors to make the combination more attractive in appearance.

Figure 2:
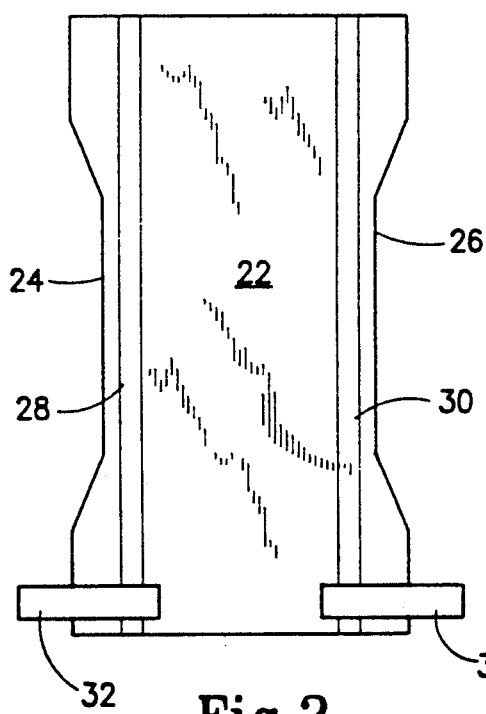
FIG. 2 is a plan view of a prior art type one-piece disposable diaper configuration.

Before proceeding to detail the inner portions of the applicant's combination, there will be described in FIG. 2 and FIG. 3 how the usual prior art combinations generally are unsatisfactory for the purpose intended by the applicant's device. In FIG. 2 there is shown a plan view of a typical prior art type one-piece, disposable diaper 22 generally used for infant children which is formed in the configuration shown and has generally straight sides 24 and 26 when constructed in the production blank. A pair of elastic side seams 28 and 30 are sewn into the sides 24 and 26 when constructed in the production blank. A pair of elastic side seams 28 and 30 are sewn into the sides 24 and 26 in order to pull the diaper tightly around the body of the baby when placed thereon. A pair of self-stick fastener tapes 32 and 34 are applied at the one end of the diaper and are used to hold the diaper on the body of the baby.

Figure 3:
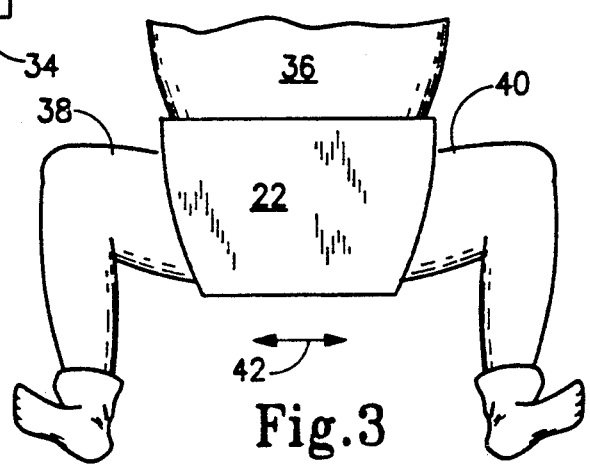
FIG. 3 is a side view showing a typical diaper positioned on an infant or a young child.

Referring to FIG. 3 there is shown a side view of a typical prior art type diaper 22 positioned on an infant's body 36. Because of the rectangular shape of the prior art diaper 22 as shown in FIG. 2 the bulk of the diaper body between the legs tends to force the infant's legs 38 and 40 outwardly in the direction shown by the arrow 42 in the crotch of the baby. From this it can be seen that the prior art type construction does not provide for a simplified fit in the crotch area to minimize this condition. It is felt that a continued use of this type of prior art diaper can be a deleterious effect on the baby's lower extremities in the area of the legs 38 and 40 since the legs were not made to be forced outwardly in this manner due to the bulk of diaper material contained in the crotch area.

Referring now to FIG. 4 of the drawing there is shown a plan view of the production blank for the applicant's new and novel combination diaper/training pant used for infants, children and adults. In FIG. 4 there is shown the inside of the diaper in the production blank form which comprises the before-mentioned outer front water-resistant portion 20 shaped like a pair of training pants. An outer rear surface 44 formed of water-resistant material and shaped like a pair of training pants also is joined to the outer front portion 20 with the two portions so joined having a generally hourglass configuration and form a water-resistant mid-portion 46 when the two outer portions 20 and 44 are joined together.

An inner front water-absorbing portion 48 is joined to the outer front water-resistant portion 20 and is shaped like a pair of training pants also. An inner rear water-absorbing portion 50 is joined to the outer water-resistant portion 44 and is shaped like a pair of training pants also. The two inner front and rear water-absorbing portions 48 and 50 so joined have a generally hourglass configuration and form a water-absorbing mid-portion 52 when the two inner portions are joined together. The joining of the inner portions of to the outer portions is accomplished by sewing, adhesive joining or some other known joining means within the art. A separate inner padding is positioned between the outer water-resistant portions 20 and 44 and the inner water-absorbing portions 48 and 50 and is joined thereto with the inner padding also being formed in a generally hourglass configuration. However, it should be appreciated that the inner padding could be smaller in configuration than the outer water-resistant portions and the inner water-absorbing portions without departing from the scope of this invention.

Figure 5:
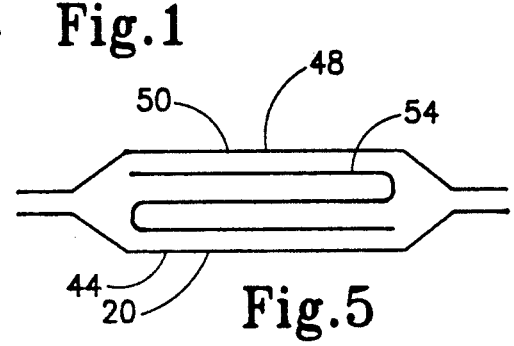
FIG. 5 is a sectional view, taken along line 5—5 of FIG. 4.

Reference should be made to FIG. 5 which is a sectional view, taken along line 5—5 of FIG. 4 showing in detail the inner padding 54 which would be water-absorbent and which would be constructed in the appropriate thickness desired for the particular type of person using the combination. In FIG. 5 the inner water-absorbing pad 54 is shown folded to provide three thicknesses and it is within the spirit and scope of the invention that it could be also a single thickness, a double thickness and more than three thicknesses as desired.

Figure 6:
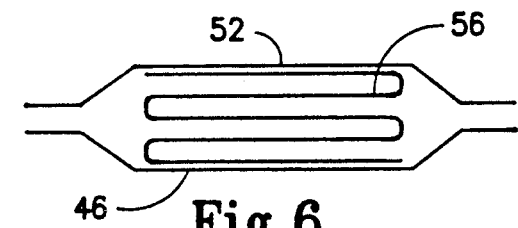
FIG. 6 is a sectional view, taken along line 6—6 of FIG. 4.

Referring to FIG. 6 of the drawing there is shown a sectional view, taken along line 6—6 of FIG. 4 showing the inner water-absorbing padding 56 which would be positioned within the mid-portion or crotch area of the diaper. In FIG. 6 the inner water-absorbing padding 56 has been shown as folded to provide five thicknesses of water-absorbing material in this area and it could also have more or less thicknesses as desired according to the particular individual for which the combination is designed. The inner water-absorbing padding 54 and 56 can also be formed as a one-piece construction formed in a general hourglass configuration and may also be formed in the three-piece configuration as shown in FIG. 4 with the break-off between the separate pieces of inner water-absorbing padding being shown generally by the dotted lines 58 and 60 in the drawing. The break-off between the inner water-absorbing padding 48 and 50 with the inner water-absorbing padding 52 would be generally in the crotch area of the diaper within the area of the arcuate edges 62 and 64 of the crotch.

The upper edge of the diaper front may be sewn horizontally at 66 by a plurality of stitches and may also incorporate an elastic band sewn in the horizontal area of stitches at 66. The rear upper edge of the combination may also be sewn by single or multiple stitches at 68 horizontally and may also have incorporated therein an elastic tape.

When formed thusly as shown in FIG. 4 of the drawings, the applicant's combination outer water-resistant portions 20 and 44 may be formed of plastic, laminated plastic, and vinyl and other water-resistant materials within the spirit and scope of the invention. The inner water-absorbing portions 48, 50 and 52 as well as the inner water-absorbing padding 54 and/or 56 may be formed of the many known water-absorbing materials on the market today such as paper, combinations of paper and other materials within the spirit and scope of the invention.

When the applicant's production blank as shown in FIG. 4 is formed as a unit which is positioned around the user's body and then held tightly in place, it would be formed with a plurality of fastening means positioned on the sides of the combinations for fastening the portions together whenever the combination is positioned around the user's body. The fastening means may comprise a plurality of hook and loop fasteners 70 and 72, such as those sold under the trademark Velcro which are representative of the fasteners which may be used. Fasteners 70 and 72 are positioned as shown in FIG. 4 on the inner rear portion 50 to be used with a matching Velcro fastening unit 74 and 76 which would be positioned on the outer front surface 20 of the front portion. Other fastening means may be utilized such as double sided tape, a plurality of snaps and other means. It is also within the spirit and scope of the invention that the side edges 76 and 78 could be sewn together as well as side edges 80 and 82 to make a pant-type combination which would be slipped over the legs of the user. Referring to FIGS. 10 and 10A of the drawing there is shown side views of the applicant's disposable combination when formed with the side fastening such as snaps 84 between the upper end of the diaper 92 and 94 and the lower leg openings 88 and 90. When using a self-stick tape in place of the Velcro type fasteners 70, 72, 74 and 76, the self-stick tape would be applied in the approximate same positions resulting in an appearance on the side of the combination as shown in FIG. 10.

Further, by configuring diaper/training pant 10 in an hourglass configuration, the leg openings 17 each have opening axes, such as axis "B" shown in FIG. 1, formed at an acute angle $\phi$ with respect to the vertical axis "A" of the pant 10. Preferably this angle $\phi$ is forty-five degrees, although the openings may be formed so that angle $\phi$ is within a range of thirty degrees to fifty degrees.

Referring to FIG. 7 of the drawing there is shown a plan view of the outside of the production blank shown in FIG. 4 showing the positioning of the various portions of that side. As has been before mentioned, the outer water-resistant portions 20 and 44 are joined together by the outer mid-portion 46 to form the generally hourglass configuration. The plurality of Velcro-type fasteners or self-stick tape would be applied to the areas shown by the numerals 70, 72, 74 and 76. One portion of the Velcro fastener would be applied to the outer water-resistant portion 20 as shown by the solid area numbered 74 and 76 while the matching portion of the Velcro fastener would be applied to the inner water-absorbing portion 50 as shown by the numerals 70 and 72 shown in dashed lines.

Indicia 96, 97, and 98 designating a name of the user of the combination and other indicia may be applied to the outer water-resistant portions 20 and 44 as desired. The indicia may be iron-on tape, stick-on tape or may be applied at the factory producing the combination. A fly front 100 may be formed in both the outer front water-absorbing portion 48 as well as in the inner front water-absorbing padding 54 or 56 should the combination be manufactured especially for use by males. The construction of the fly front would be as utilized in boys' underwear having the configuration shown in FIG. 7.

Referring now to FIGS. 8 and 9 of the drawings there is shown in FIG. 8, a partial sectional view, taken along line 8—8 of FIG. 4 showing the positioning of the Velcro-type fasteners 72 on the inner water-absorbing portion 50 of the combination. One-half of the Velcro-type fasteners would be constructed as is known in the art having a series of loops as shown in FIG. 8 at the numeral 72 while the other half of the fasteners would be formed with a series of gripping curled fingers as shown in FIG. 9 of the drawing at the numeral 76. By pushing the two mating pieces of the Velcro fastener together, a tight joining engagement is made at the respective sides of the unit sufficient to hold the combination on the user of the applicant's invention.

By constructing the combination in the general hourglass configuration, the mid or crotch portions 46 and 52 of the combination may be formed with a predetermined radius 102 and 104 forming the crotch area and may also be formed in a generally V or U-shaped configuration to minimize the amount of material in the crotch area shown by the numeral 106. These minimal amounts of material should be sufficient for water-absorption in this area and yet not in great amounts to cause the user's legs 38 and 40 to be forced apart by virtue of the bulky amount of material in this area. This can be designed according to the particular person for which the combination is designed and would be different for males as opposed to females and also would be different for babies as opposed to younger children and older adults.

In the general configuration shown in the drawing FIGS. 4 and 7 for the applicant's basic combination and by varying the particular dimensions of the unit, a one-configuration combination may be obtained with variations in size only required for the different ages of individuals using the unit. In this manner a mother is not required to stock a plurality of different types of devices for her child such as a separate disposable diaper and a separate training pant and is able to use the same combination both in daytime and in the evening. This adaptability then makes the applicant's combination a more suitable and universal combination which would cause less trauma and confusion to the child using the device since a different feel of device is not placed on the child in the morning as compared to the nighttime device.

By the use of appropriate indicia such as indicia 12, 14, 96, 97, and 98 the applicant's basic combination may be varied to make it more pleasing and attractive to the user should the user be a teenage or older person having incontinent problems or possibly mental problems causing incontinence thus requiring the applicant's device. The use of the various indicia either singly or in combination and the use of various colors for the outer water-resistant portions can make the applicant's basic combination a much more pleasing and acceptable combination for the older-type child or adult. While the fly front 100 may be desirable for younger children requiring potty training, it may not be desirable in the event the male child is mentally unbalanced and when potty training would not be prescribed. In that case the male child as well as the female child of this condition would use the same basic combination without the fly front.

Referring now to FIGS. 11 through 15 of the drawing there is shown in detail the applicant's universal two-piece washable combination diaper/training pant 108 for infants, children and adults. In the before-described basic combination shown in FIGS. 4 through 10A of the drawing there was shown and described the applicant's one-piece, disposable combination. By one-piece, it is meant that the entire combination is sewn or fastened together to form a complete unit which is disposable as is with the one-piece configuration being constructed of the various outer water-resistant portions and inner water-absorbing portions as well as inner water-absorbing padding positioned and sewn or laminated together as shown in the drawings. In FIGS. 11 through 15 the applicant's two-piece construction is shown which comprises an outer water-resistant portion and a separate removable water-absorbing inner padding positioned within the outer water-resistant portion. The separate removable inner water-absorbing padding may be disposable and may also be washable within the spirit and scope of the invention. The outer water-resistant portion 110 shown in FIG. 11 may be formed of the usual water-resistant material such as plastic, laminated plastic, vinyl and other suitable materials and may be formed white, solid colors or combinations of colors within the spirit and scope of the invention to make the outer appearance more desirable to the user. A plurality of indicia 112 may be positioned on the outer water-resistant portion 110 designating various objects such as flowers, animals and the like. Other indicia 114 may be applied to the outer water-resistant portion 110 to designate the user's name. The indicia 112 and 114 may be iron-on tape, self-stick tape and may also be applied at the factory producing the basic combination.

Referring now to FIG. 12 of the drawing there is shown a plan view of the inside of the applicant's two-piece combination shown in FIG. 11 showing the separate insertable and removable water-absorbing inner padding 116 which is positioned partly within two pockets 118 and 120 and running the entire transverse width of the unit. The inner padding 116 may be of the water-absorbing type hereinbefore described such as paper, combinations of paper and other materials and may also be formed of cotton and other washable materials within the spirit and scope of the invention. When formed of the paper material the inner padding 116 would be disposable and when formed of cotton or other washable materials the inner padding would be removed upon becoming wet and would be washed and re-used for many repeated usages.

Figure 15:
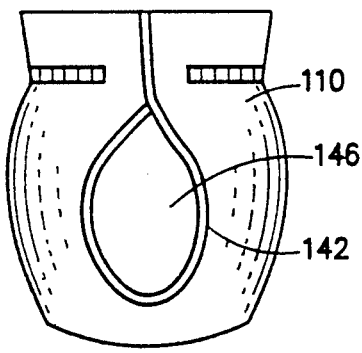
FIG. 15 is a side view, taken along line 15—15 of FIG. 11 showing the appliant's new and novel combination as it would be positioned over a user's body.

Referring now to FIG. 14 of the drawing there is shown the production blank for the outer portion 110 of applicant's two-piece, washable combination diaper/training pant for infants, children and adults which comprises a generally rectangular shaped outer water-resistant portion 110 having a central section 122 and two outer ends 124 and 126 separated by the dashed lines 128 and 130 used to indicate the line of separation. The central section 122 also contains two outer sides 132 and 134 along which are sewn the first elastic means 136 and 138 as shown in FIG. 14. The first elastic means 136 and 138 would be sewn along the outer sides 132 and 134 while being stretched so that upon release of the stretched elastic means, the outer sides 132 and 134 would gather or curl the outer sides to a condition as shown in FIG. 12 of the drawing at the numerals 140 and 142. The gathered edges 140 and 142 then give the applicant's basic production blank a generally hourglass configuration pulling the central portion or crotch area of the combination inwardly as shown by the dimension arrow 144. This then also provides a gathered leg area as shown in FIG. 15 by the numeral 146 making the combination fit tightly around the legs of the user which would protrude through the leg area 146.

The two outer ends 124 and 126 also contain a second elastic means 150 and 152 sewn on a portion of the two outer sides 154 and 156. A third elastic means 158 and 160 is sewn on a portion near the two outer ends 154 and 156 as shown in FIG. 14. The second and third elastic means 150, 152, 158 and 160 are sewn while in the stretched position so that upon release of the sewn stretched elastic means the two outer ends 154 and 156 will gather in an arcuate shape making a distinctive appearing gathered edge on the combination diaper/training pant. The gathered portion 162 is shown in FIG. 11 of the drawing and gives the top of the applicant's combination a distinctive appearing feature making it very decorative due to the gathering in the area of the elastic means. The sewn elastic means 158 is shown dashed in FIG. 11 of the drawing and forms part of the decorative appearance of the upper portion of the applicant's combination.

The rear of the combination would be virtually identical to the view shown in FIG. 11 with the gathering being accomplished by the sewn second elastic means 152 and the third elastic means 160.

After the various elastic means 136, 138, 150, 152, 158 and 160 are sewn into the central section 122 and the ends 124 and 126, then the outer ends 124 and 126 would be rotated about the imaginary dotted lines 128 and 130 to form the pockets 118 and 120 before mentioned. A sewn stitch would be applied as shown by the dashed lines in FIG. 12 at the edges 164, 166, 168 and 170 to make the pockets 118 and 120 suitable to receive the inner padding 116.

In FIG. 13 there is shown a cross-sectional view, taken along line 13—13 of FIG. 12 showing how the inner pockets 118 and 120 are formed and showing in enlarged detail how the second elastic means 150 and 158 along with the second elastic means 152 and 160 are positioned on the interior portion of the outer water-resistant portion 110.

The production blank thus described may then have applied thereto some fastening means which would be fixedly attached to a portion of the outer sides. The fastening means are shown in FIG. 12 of the drawing as the numerals 172, 174, 176 and 178 and may comprise Velcro fasteners of the type hereinbefore described, double sided tape, a plurality of snaps and other fastening means within the spirit and scope of the invention.

When formed thusly the applicant's new and novel universal two-piece combination may be sold as a unique combination having an outer washable water-resistant portion 110 with an inner padding 116 that may be designed to be either disposable or washable. By providing the outer water-resistant portion 110 in white or various colors in combination with the decorative, distinctive, gathered appearance in the area 162 and with indicia 112 and/or 114 applied to the combination, there is available a distinctive appearing under-garment which is functional also in design. By the use of the gathered edges 140 and 142 forming an acruate shape or hourglass shape in this area there is provided also a tightly fitted under-garment which will not leak in the area of the leg openings. By varying the length and width of the garment and the appropriate thickness of inner padding 116, the basic garment may be used by a mother for various children without having to stock different types of garments. For example by purchasing only a limited supply of inner paddings 116 in various thicknesses, the same outer garment can be used for a plurality of the mother's children that have different incontinence problems. For example a heavy wetter could use the same outer garment 110 in combination with a much heavier padding 116 while a lighter wetter child may use the outer garment 110 in combination with a much smaller thickness padding 116.

Figures 16, 17:
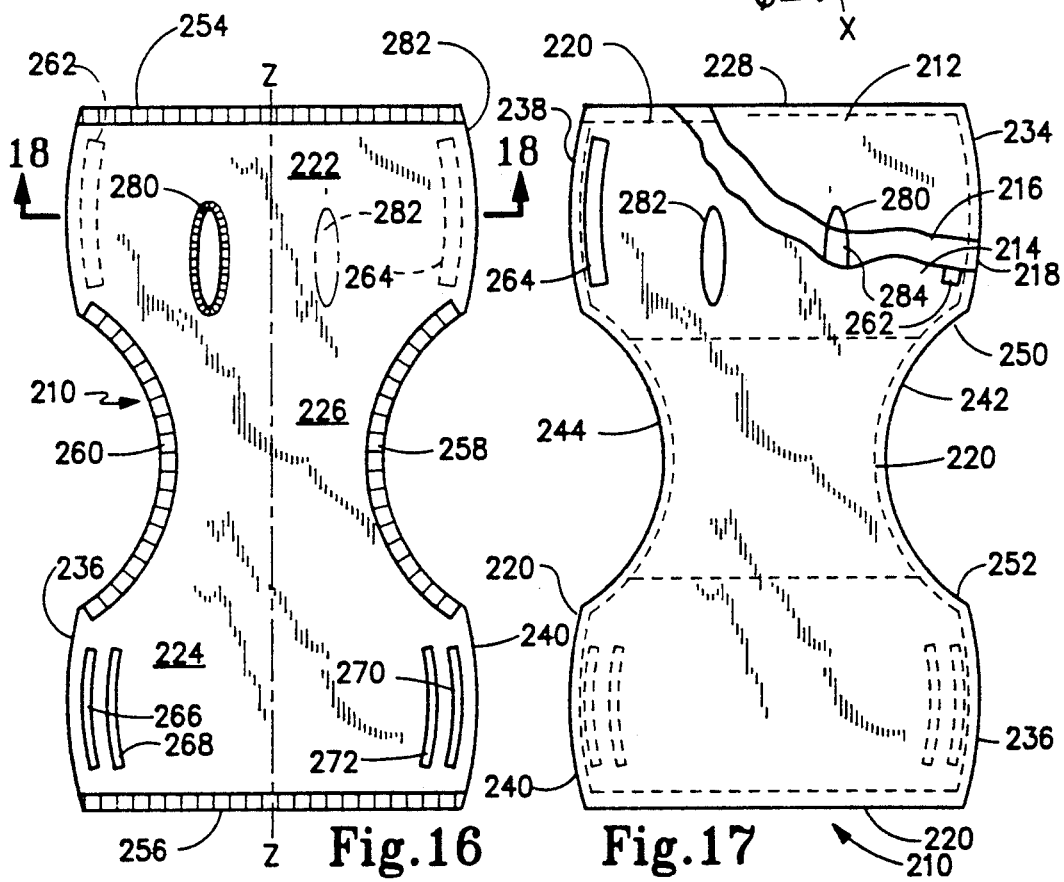
FIG. 16 is a front plan view of the outside of an alternate embodiment of the one-piece disposable diaper/training pant according to the present invention, prior to use.
FIG. 17 is a back plan view of the diaper/training pant shown in FIG. 16.
Figure 18:
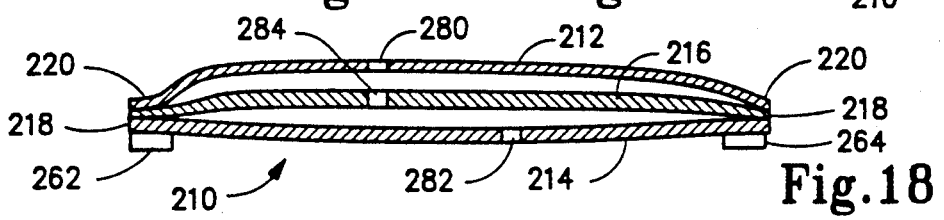
FIG. 18 is a cross-sectional view taken about line 18—18 of FIG. 16.

FIGS. 16–19 show an embodiment of the present invention which is an alternate embodiment to the preferred form (shown in FIGS. 1 and FIGS. 4–10A). As is depicted in FIGS. 16–19, a diaper/training pant 210 has an outer water-resistant panel 212, a water-absorbent inner panel 214 and a water-absorbent intermediate panel 216. Panel 212 may be formed of a thin plastic material, commonly used on disposable diapers, and may also be laminated plastic, vinyl and the like. Panels 214 and 216 are preferably formed of an expanded paper material, again similar to disposable diapers. Each of panels 212, 214 and 216 have a common hourglass configuration, as is shown in FIGS. 16 and 17, and these panels are joined to one another along a common perimeter 218 by any convenient manner, such as stitching 220 as is shown in FIGS. 17 and 18. Diaper/training pant 210, when so constructed, has a front portion 222, a rear portion 224 and a mid portion 226, with each of panels 212, 214 and 216 having corresponding front, rear and mid portions to so construct pant 210.

Figure 19:
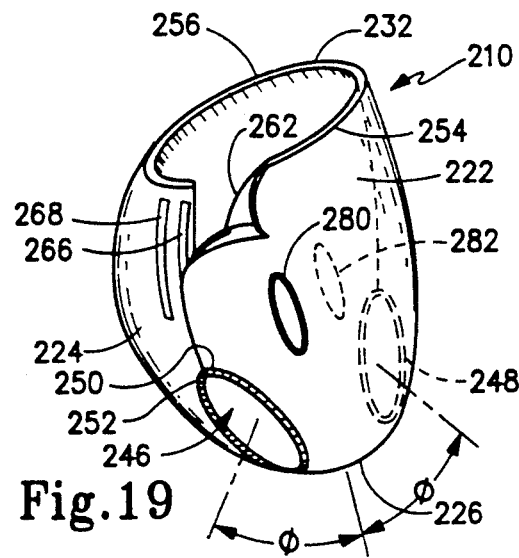
FIG. 19 is a perspective view of the diaper/training pant of FIGS. 16-18, shown in an attached position as it would be worn.

When configured for wear on the human body, as is shown in FIG. 19, top forming edge portions 228 and 230 define a top edge 232 which will surround the waist of the wearer. Edge portions 234 and 236 may be overlapped with one another, as is shown in FIG. 19, to form a partible hip section on the right side of the body. Similarly, side edge portions 238 and 240, form a partible hip section on the left side of the body, when diaper/training pant 210 is configured as a unit for being worn. Further, as thus configured, the arcuate edge portions 242 and 244 each close on itself to form respective leg openings 246 and 248, respectively. To this end and by way of example, end points 250 and 252 of arcuate edge portion 242 will contact one another to form leg opening 246.

To help position and retain diaper/training pant 210 on the body, as well as to help prevent the leakage of fluid waste material from the diaper/training pant, top forming edge portions 228 and 230 are provided with elastic bands 254 and 256, respectively. Likewise, arcuate edges 242 and 244 are provided with elastic bands 258 and 260, respectively. Thus, the raised opening defined by top edge 232 and each of leg openings 246 and 248 are completely surrounded by elastic material which will expand to accommodate the trunk and legs of the wearer. Further, by providing tapered midportion 226, the axis "C" of leg opening 246 and axis "D" of opening 248 are oriented at an acute angle of approximately forty-five degrees with respect to vertical axis "X" of diaper/training pant 210 when it is configured as a unit to be worn, all as is shown in FIG. 19. Thus, angle $\phi$ which describes the angle between vertical axis "X" and each of axes "C" and "D" is preferrably forty-five degrees, but may conveniently be selected to be between thirty degrees and fifty degrees. This orientation is in contrast to the substantial 90 degree orientation shown in FIGS. 2 and 3 which results from the folding of a generally rectangular diaper blank. It should be also understood that the orientation of axes "C" and "D" is controlled by the curve radius of each of arcuate edges 242 and 244 so that the greater the radius of curvature, the larger angle $\phi$ becomes.

In order to secure diaper/training pant 210 around the body, it is necessary to releasably fasten side edges 234 and 236 to one another and to fasten side edges 238 and 240 to one another. To this end, inner panel 214 is provided with adhesive strips, such as adhesive tape 262 attached along the margin adjacent and parallel to side edge 234 and adhesive tape 264 attached adjacent and parallel to side edge 238. These bands are oriented on the interior of the configured unit shown in FIG. 19. Mating adhesive tape bands are attached along side edges 236 and 240 on outer panel 212 so that these bands may adhere to bands 262 and 264. As is shown in FIG. 16 a first pair of tape bands 266 and 268 are formed on the margin of rear portion 224 parallel and adjacent to side edge 236. Tape band 262 is thus adapted to adhere to either of tape bands 266 and 268. Likewise, a pair of tape bands 270 and 272 are provided parallel to and adjacent side edge 240 on the exterior surface of rear portion 224 of panel 212 so that tape band 264 may be selectively adhered to either of tape bands 270 and 272.

It should be appreciated that the pairs of tape bands 266, 268 and pair 270, 272 are provided for two purposes. First, by providing these pairs of bands, the effective size of the diaper/training pant 210 may be adjusted. Further, should the diaper/training pant 210 be worn for a period of time after which it is removed to allow the wearer to eliminate waste, the pant may be reattached even should the adhesive properties of one of the pairs of bands 266, 268 and 270, 272 lose its adhesive properties.

In order to further construct diaper/training pant 210 in a manner that more nearly resembles a traditional underpant for the male user, fly openings are provided in each of layers 212, 214 and 216 at front portion 222. As is best shown in FIGS. 16-18, panel 212 is provided with an outer fly opening 280, panel 214 is provided with an inner fly opening 282 and intermediate panel 216 is provided with intermediate fly opening 284. Each of these fly openings is symmetric about line "Z" shown in FIG. 16 and, although these fly openings could be arcuate in configuration, they are preferably formed parallel to line "Z" which defines the longitudinal axis of the pant blank. By constructing the fly openings 280, 282 and 284 in this manner, it should be appreciated that the assembly of diaper/training pant 210 may be facilitated and may be accomplished at reduced manufacturing cost. Specifically, with this configuration, both absorbent inner and intermediate panels 214 and 216 are constructed identically but are oriented with respect to one another so that their respective fly openings 282 and 284 are staggered. Once this is done, the resultant assembled unit may be placed on outer panel 212 of the fly opening of the absorbent panel which accordingly becomes intermediate panel 216 will automatically align with fly opening 280. This assembly may be then joined along perimeter 218 and the elastic bands and the adhesive tape bands may be secured thereto.

From the foregoing it can be seen that there has been provided by the applicant's invention and modification thereof a universal combination diaper/training pant for children and adults which may be made in the various configurations and sold as a one-piece or two-piece configuration that may be disposable or washable as desired. The applicant's invention and modification allows the parent of the child to purchase and use only one garment throughout the life of the garment and reduces the number of garments that must be stocked by the mother. By the application of the various indicia to the various combinations, the garments are made much more attractive and desirable for the child to wear thereby resulting in less havoc to the mother when applying the garment to the child or mentally disturbed person having incontinence problems.

From the foregoing it can be seen that changes may be made in the basic invention and modification of the invention such as variations in the dimensions and positioning of the various snaps, fasteners, pads and other variations without departing from the spirit and scope of the invention. The applicant is not to be limited to the exact embodiments shown which have been given by way of illustration only.

I claim:

1. A disposable incontinent garment adapted to be worn on the body by incontinent persons, comprising an outer fluid resistant panel, a wettable inner absorbent panel and a fluid absorbent intermediate panel positioned between said inner and outer panels, said outer and inner panels having a common hourglass shape and having a perimeter formed by first and second top edge forming portions, arcuate edge portions defining a midportion of reduced width and side edge portions extending between the ends of each arcuate edge portions and top edge forming portions, said outer and inner panels joined along said perimeter and configurable in a position during wear such that the wettable inner absorbent panel is against the body and wherein the top edge forming panels will form a waist edge and respective pairs of said side edges will overlap one another to form partible hip sections so that arcuate edge portions each closes on itself to form a leg opening, fastening means along margin portions adjacent said side edges for releasably securing the respective pairs of overlapped side edges together, said inner and said intermediate panels being formed substantially the same, and each including a fly opening offset with respect to a longitudinal axis when the incontinent garment is joined during wear whereby the intermediate and inner panels are oriented with their fly openings staggered with respect to said longitudinal axis, and said outer panel having an outer fly opening offset with respect to the longitudinal axis and which outer fly opening is coextensive with the fly opening of the intermediate panel.

* * * * *